United States Patent
Clifford et al.

(10) Patent No.: US 10,626,436 B2
(45) Date of Patent: Apr. 21, 2020

(54) METHOD OF DETERMINING A COMPOSITIONAL OR FUNCTIONAL CHARACTERISTIC OF A CELL CULTURE MEDIA

(71) Applicant: Valitacell Limited, Co. Dublin (IE)

(72) Inventors: Jerry Clifford, Tralee (IE); David James, Sheffield South Yorkshire (GB); Ben Thompson, Sheffield South Yorkshire (GB)

(73) Assignee: Valitacell Limited, Co. Dublin (IE)

( * ) Notice: Subject to any disclaimer, the term of this patent is extended or adjusted under 35 U.S.C. 154(b) by 0 days.

(21) Appl. No.: 15/562,403

(22) PCT Filed: Apr. 1, 2016

(86) PCT No.: PCT/EP2016/057283
§ 371 (c)(1),
(2) Date: Sep. 27, 2017

(87) PCT Pub. No.: WO2016/156604
PCT Pub. Date: Oct. 6, 2016

(65) Prior Publication Data
US 2018/0282779 A1 Oct. 4, 2018

(30) Foreign Application Priority Data
Apr. 1, 2015 (EP) .................................... 15162281

(51) Int. Cl.
*C12Q 1/04* (2006.01)
*C12N 5/00* (2006.01)
*G01N 33/50* (2006.01)

(52) U.S. Cl.
CPC .............. *C12Q 1/045* (2013.01); *C12N 5/00* (2013.01); *C12N 5/0018* (2013.01); *G01N 33/502* (2013.01)

(58) Field of Classification Search
CPC ......... C12N 5/0018; C12N 5/00; C12Q 1/045
USPC ........................................................ 506/10
See application file for complete search history.

(56) References Cited

U.S. PATENT DOCUMENTS

| | | |
|---|---|---|
| 5,328,985 A | 7/1994 | Sano et al. |
| 5,660,991 A | 8/1997 | Lakowicz et al. |
| 7,427,473 B2 | 9/2008 | Strovel et al. |
| 8,492,144 B2 | 7/2013 | Dorai et al. |
| 2001/0051331 A1 | 12/2001 | Nakayama et al. |
| 2002/0150890 A1 | 10/2002 | Nakayama et al. |
| 2003/0235813 A1 | 12/2003 | Luyten et al. |
| 2005/0095655 A1 | 5/2005 | Montero-Julian et al. |
| 2005/0204418 A1 | 9/2005 | Jung et al. |
| 2006/0105397 A1 | 5/2006 | Cullum et al. |
| 2007/0184447 A1* | 8/2007 | Strovel ................ C12Q 1/6886 435/6.1 |
| 2009/0117647 A1 | 5/2009 | Buddhi Srinivasa et al. |
| 2009/0197243 A1 | 8/2009 | Rieder et al. |
| 2009/0287320 A1 | 11/2009 | MacGregor et al. |
| 2010/0152417 A1 | 6/2010 | Taki et al. |
| 2010/0033036 A1 | 12/2010 | Lambrecht et al. |
| 2010/0330036 A1 | 12/2010 | Lambrecht et al. |
| 2011/0143387 A1 | 6/2011 | Patsenker et al. |
| 2012/0190073 A1 | 7/2012 | Chartrain et al. |
| 2014/0199728 A1 | 7/2014 | Du et al. |
| 2016/0139109 A1 | 5/2016 | Thompson et al. |
| 2017/0017891 A1 | 1/2017 | Thompson et al. |
| 2017/0030894 A1 | 2/2017 | Thompson et al. |
| 2017/0160286 A1 | 6/2017 | Thompson et al. |
| 2019/0011437 A1 | 1/2019 | Clifford et al. |

FOREIGN PATENT DOCUMENTS

| | | |
|---|---|---|
| CN | 101186880 A | 5/2008 |
| CN | 201569914 U | 9/2010 |
| CN | 102220239 A | 10/2011 |

(Continued)

OTHER PUBLICATIONS

"Carmichael et al. "Chemosensitivity testing of human lung cancer cell lines using the MTT assay." British Journal of Cancer 57 .6 ( 1988): 540. (Year: 1988)".

Da Cruz Meleiro, et al., "Non-Linear Multivariable Predictive Control of an Alcoholic Fermentation Process Using Functional Link Networks", Brazilian Archives of Biology and Technology, Instituto De Tecnologia Do Parana, BR, vol. 48, No. Special, Jun. 2005, pp. 7-18.

(Continued)

*Primary Examiner* — Karla A Dines
(74) *Attorney, Agent, or Firm* — Hamilton, Brook, Smith & Reynolds, P.C.

(57) ABSTRACT

A method of determining variation between a query cell culture media and a reference cell culture media is provided. The method comprises the steps of incubating a reference cell with an aliquot of the query culture media and at least three chemical cell stressors in wells of a microtitre plate and determining an environmental response of the reference cell in the presence of the query cell culture media and each of the plurality of chemical cell stressors. A query cell culture media specific environmental response fingerprint is generated comprising the plurality of chemical cell stressor specific environmental responses. The query cell culture media-specific environmental response fingerprint is compared with a reference media-specific environmental response fingerprints corresponding to a reference cell culture media and generated using the reference cell. Variation between the query cell culture media and the reference cell culture media is then determined based on the level of correlation between the query cell culture media-specific environmental response fingerprint and the reference media-specific environmental response fingerprints.

8 Claims, 5 Drawing Sheets

(56) References Cited

FOREIGN PATENT DOCUMENTS

| EP | 0957365 A1 | 11/1999 |
|---|---|---|
| JP | 2005337805 A | 12/2005 |
| WO | 96/13722 A1 | 5/1996 |
| WO | 199723642 A1 | 7/1997 |
| WO | 97/39326 A1 | 10/1997 |
| WO | 97/39326 A2 | 10/1997 |
| WO | 01/81895 A2 | 11/2001 |
| WO | 02/37102 A2 | 5/2002 |
| WO | 2006/135992 A1 | 12/2006 |
| WO | 2008/141317 A1 | 11/2008 |
| WO | 2009/078876 A1 | 6/2009 |
| WO | WO 2013/144359 A2 | 10/2013 |
| WO | 2014/207166 A1 | 12/2014 |
| WO | 2015/113704 A1 | 8/2015 |
| WO | 2015/150551 A1 | 10/2015 |
| WO | 2016/008671 A1 | 1/2016 |
| WO | 2016/156604 A1 | 10/2016 |
| WO | 2017/103210 A1 | 6/2017 |

OTHER PUBLICATIONS

Gao et al. "Powerful and prolonged protection of human retinal pigment epithelial cells, keratinocytes, and mouse leukemia cells against oxidative damage: the indirect antioxidant effects of sulforaphane." Proceedings of the National Academy of Sciences 98.26(2001): 15221-15226 (Year: 2001).

Godoy-Silva, et al., "Physiological Responses of CHO Cells to Repetitive Hydrodynamic Stress", Biotechnology and Bioengineering, vol. 103, No. 6, Aug. 15, 2009, pp. 1103-1117.

Jostock, et al., "Combination of the 2A/Furin Technology with an Animal Component Free Cell Line Development Platform Process", Applied Microbiology and Biotechnology, vol. 87, No. 4, May 12, 2010, pp. 1517-1524.

Legmann, et al., "A Strategy for Clone Selection Under Different Production Conditions", Biotechnology Progress, vol. 27, No. 3, May 29, 2011, pp. 757-765.

Nakatsu, et al., "Evaluation of Action Mechanisms of Toxic Chemicals Using JFCR39, a Panel of Human Cancer Cell Lines", Molecular Pharmacology (The American Society for Pharmacology and Experimental Therapeutics), vol. 72, No. 5, Aug. 3, 2007, pp. 1171-1180.

Non Final Office Action for U.S. Appl. No. 14/900,113 dated Aug. 8, 2018.

Notification of Transmittal of the International Search Report and the Written Opinion of the International Searching Authority, or the Declaration, consisting of 18 pages, for PCT/EP2014/063625, entitled "A Method of Determining or Predicting a Characteristic of a Cell," dated Oct. 24, 2014.

Restriction Requirement for U.S. Appl. No. 14/900,113, dated Mar. 28, 2018.

"Cell Culture Media—Addressing Variability in Dry Powder Mammalian Cell Culture Media," retrieved from the internet: URL:http://drug-dev.com/Main/Back-Issues/CELL-CULTURE-MEDIA-Addressing-Variability-in-Dry-P-598.aspx, retrieved on Jun. 10, 2015, listed posted date: Jun. 10, 2013.

Curtis, G.D.W., "A Review of Methods for Quality Control of Culture Media," Int. Journal of Food Microbiology, 2: 13-20 (Jan. 1985).

Li, B., et al., "Rapid Characterisation and Quality Control of Complex Cell Culture Media Solutions Using Raman Spectroscopy and Chemometrics," Biotechnology and Bioengineering 107(2): 290-301 (2010).

"NMR-Based Methods Fingerprinting Culture Media," Jan. 2014. retrieved from the internet: URL:http://www.spinnovation-analytical.com/images/stories/press-releases/SPI-JOB-035-article.pdf retrieved on Jun. 10, 2015.

Ryan, P.W., et al., "Prediction of Cell Culture Media Performance Using Fluorescence Spectroscopy," Anal. Chem. 82: 1311-1317 (2010).

Yen, S., et al., "Treating Cell Culture Media with UV Irradiation Against Adventitious Agents: Minimal Impact on CHO Performance," 30(5): 1190-1195 (Jul. 2014).

International Search Report and Written Opinion dated Jun. 24, 2016 of International Application No. PCT/EP2016/057283, "A Method of Determining a Compositional or Functional Characteristic of a Cell Culture Media," International Filing Date Apr. 1, 2016.

Aoyagi, S., et al. "Development of Fluorescence Change-Based, Reagent-Less Optic Immunosensor," Biosensors and Bioelectronics, 20(8): 1680-1684 (Feb. 2005).

International Preliminary Report on Patentability for International Application No. PCT/EP2016/057283, entitled "A Method of Determining a Compositional or Functional Characteristic of a Cell Culture Media," dated Oct. 3, 2017.

Xu, Jianlin, et al., "Galactose can be an inducer for production of therapeutic proteins by auto-induction using BL21 strains," Protein Expression and Purification, 83(1): 30-36 (Jun. 2005).

Chen, Min, et al., "A novel multiplexed fluorescence polarisation immunoassay based on a recombinant bi-specific single-chain diabody for simultaneous detection of fluoroquinolones and sulfonamides in milk," Food Additives & Contaminants, Part A, vol. 31(12): 1959-1967 (Nov. 13, 2014).

Dorai, Haimanti, et al., "Combining high-throughput screening of caspase activity with anti-apoptosis genese for development of robust CHO production cell lines," Biotechnology Progress, 26(5): 1367-1381 (Sep. 2010).

International Search Report and the Written Opinion for PCT/EP2014/078340, entitled "A Method of Predicting Relative Fed Batch Production Titer of a Panel of Clonally-Derived Producer Cells," dated Mar. 23, 2015.

Zhang, S., et al., "Fluorescence Polarisation Immunoassay Based on Monoclonal Antibody for the Detection of Sulphamethazine in Chicken Muscle," International Journal of Food Science and Technology, 42(1): 36-44 (Jan. 1, 2007).

International Preliminary Report on Patentability for Int'l Application No. PCT/EP2014/078340, entitled: "A Method of Predicting Relative Fed Batch Production Titer of a Panel of Clonally-Derived Producer Cells," dated May 24, 2016.

International Preliminary Report on Patentability for Int'l Application No. PCT/EP2014/063625, entitled: "A Method of Determining or Predicting a Characteristic of a Cell," dated Dec. 29, 2015.

International Preliminary Report on Patentability for Int'l Application No. PCT/EP2015/057392, entitled: "A Method of Predicting Phenotypic Instability in a Cell," dated Oct. 4, 2016.

Wang, Z-H., et al., "Analysis of Sulfamethazine by Fluorescence Polarization Immunoassay," Chinese Journal of Analytical Chemistry, 35(6): 819-824 (Jun. 2007).

Gokulrangan, G., et al., "DNA Aptamer-Based Bioanalysis of IgE by Fluorescence Anistropy," Analytical Chemistry, 77(7): 1963-1970 (Apr. 1, 2005).

Lea, W.A., et al., "Fluorescence Polarization Assays in Small Molecule Screening," Expert Opinion on Drug Discovery, 6:(1): 17-32 (Jan. 2011).

Moerke, N.J., "Fluorescence Polarization (FP) Assays for Monitoring Peptide-Protein or Nucleic Acid-Protein Binding," Current Protocols in Chemical Biology, vol. 1: 1-15 (Dec. 2009).

Restriction Requirement for U.S. Appl. No. 15/114,359, dated Sep. 10, 2018.

Cudré-Mauroux, C., et al., "Lentivector-Mediated Transfer of Bmi-1 and Telomerase in Muscle Satellite Cells Yields a Duchenne Myoblast Cell Line with Long-Term Genotypic and Phenotypic Stability," Human Gene Therapy, 14(16): 1525-1533 (2003).

Gignac, S.M., et al., "Multiparameter approach in the identification of cross-contaminated leukemia cell lines," Leukemia & Lymphoma, 10(4-5): 359-368 (1993).

Schwartz, R., et al., "Heterogeneity of glycoprotein synthesis in human tumor cell lines," European Journal of Cancer and Clinical Oncology, 22(3): 273-281 (1986).

International Search Report and the Written Opinion for PCT/EP2015/057392, entitled "A Method of Predicting Phenotypic Instability in a Cell," dated Jul. 21, 2015.

(56) References Cited

OTHER PUBLICATIONS

Gunther J.C., et al., "Process monitoring and quality variable prediction utilizing PLS in industrial fed-batch cell culture," Journal of Process Control, 19: 914-921 (2009).
Kim, J.Y. et al., "CHO cells in biotechnology for production of recombinant proteins: current state and further potential," Appl. Microbiol. Biotechnol., 93:917-930 (2012).
Non-Final Office Action for U.S. Appl. No. 15/114,359, dated Feb. 25, 2019.
Final Office Action for U.S. Appl. No. 14/900,113, dated Mar. 1, 2019.
Non-Final Office Action for U.S. Appl. No. 15/301,319, dated Jun. 14, 2019.
Fowler, et al., "Self-Assembled Layer of Thiolated Protein G as an Immunosensor Scaffold," Anal. Chem., 79, (2007), p. 350-354 (Year: 2007).
Li, et al., Cell culture processes for monoclonal antibody production, Landes Bioscience, 2(5), (2010), p. 466-477 (Year: 2010).
Sayoko, et al., Machine translation of JP2005337805 (English Translation of the Disclosure), obtained via Dialog on Jul. 11, 2019 at [https://dialog.proquest.com.professional/japanpatentsft/docview/1390751074/16B46B58CBE203E90EE/2?] (Year: 2005).
Non-Final Office Action for U.S. Appl. No. 14/900,113, dated Oct. 21, 2019.
Notice of Allowance for U.S. Appl. No. 15/301,319, entitled "A Method Of Predicting Phenotypic Instability in a Cell," dated Jan. 13, 2020.

\* cited by examiner

METHOD OF DETERMINING A COMPOSITIONAL OR FUNCTIONAL CHARACTERISTIC OF A CELL CULTURE MEDIA

This application is the U.S. National Stage of International Application No. PCT/EP2016/057283, filed Apr. 1, 2016, which designates the U.S., published in English, and claims priority under 35 U.S.C. §§ 119 or 365(c) to EP Application No. 15162281.8, filed Apr. 1, 2015. The entire teachings of the above applications are incorporated herein by reference.

INTRODUCTION

The invention relates to a method of determining a compositional or functional characteristic of a cell culture media, in particular a cell culture media employed for culturing mammalian producer cells in a biopharmaceutical production process.

BACKGROUND TO THE INVENTION

Many biopharmaceuticals are produced by genetically modified single cell organisms, known as producer cells. A well established system has been established for producing biopharmaceuticals using mammalian producer cells. The first step involves deriving a high-producing cell line that is suitable for large scale production, a process that involves first transfecting, cloning and then characterising a large number of cell lines. This is an expensive and labour and time intensive process, lasting up to 12 months. Once a gene of interest has been transfected and selection pressure applied using the expression system of choice, the next step involves selection and isolation of cells with acceptable growth and recombinant protein production rate. Cells are cultured and expanded to give clonal populations and once typically hundreds of clonal polulations are established, cell line characterisation takes place.

During the biopharmaceutical production process, the clones are incubated with a cell culture media that is tailored for the specific production process. These media are generally produced commercially in large batches (lots), however due to the complexity of the production process and large number of variables involves, it is not uncommon for there to be compositional variation between batches of the same cell culture media product, which can result in changes of performance in terms of modified growth response or production titer response or product quality attributes or host cell protein production when the media is employed in a biopharmaceutical production process. Currently, the method of testing lots of cell culture media involves an extended culture in the media of interest in parallel with a previous batch. Growth and productivity are compared, and ocassionally product quality would be compared too. Subtle differences may take a while to manisfest themselves and thus may not be apparent in such a short time period and would require a number of generations. This would not be observed with standard methods. A media which is functionally different from its comparitor would be a cause for concern even though other attributes may be consistent. This underlying 'latent difference' could cause productivity, instability or other issues down the line, especially when the product is manufactured at scale in a bioreactor over a long time period over multiple generations.

The problem of variability in cell culture media, especially culture media employed in the biopharmaceutical industry, is recognised in the literature and discussed in a number of documents. For example, Boyan Li et al (Biotechnology and Bioengineering, 107(2), 290-301) discuss the problem and disclose the use of Raman spectroscopy combined with chemometrics as a means of rapid characterisation and quality control of complex cell culture media solutions. However, Raman spectrometers and lasers are highly expensive and require specially trained personnel for accurate and reproducible operation. Girard (www.spinnovation-analytical.com/images/stories/press-releases/SPI-JOB-035-article.pdf) discloses the use of nuclear magnetic resonance (NMR) and custom-design NMR databases to rapidly identify and quantitate the compounds present in fermentation media. While this technique would be very accurate and sensitive, NMR machines are extremely expensive and require highly skilled operate. The article "Cell Culture Media—addressing variability in dry powder mammalian cell culture media" (www.drug-dev.com/Main/Back-issues/CELL-CULTURE-MEDIA-Addressing-Variability-in-Dry-P-598.aspx) discusses the problem in variability specifically between different lots of the same brand of media, and discloses a number of benchmarking study that was performed using different analytical methods including a technique that employs NMR, UPLC and PCA analysis to determine differences between different lots of media. As discussed above, while NMR is extremely sensitive and acurate, NMR machines are very expensive and require highly specialised personnel to operate. In addition, these methods are restricted to analysing the chemical constitution of the media.

It is an object of the invention to overcome at least one of the above-referenced problems.

STATEMENTS OF INVENTION

Figure 1:
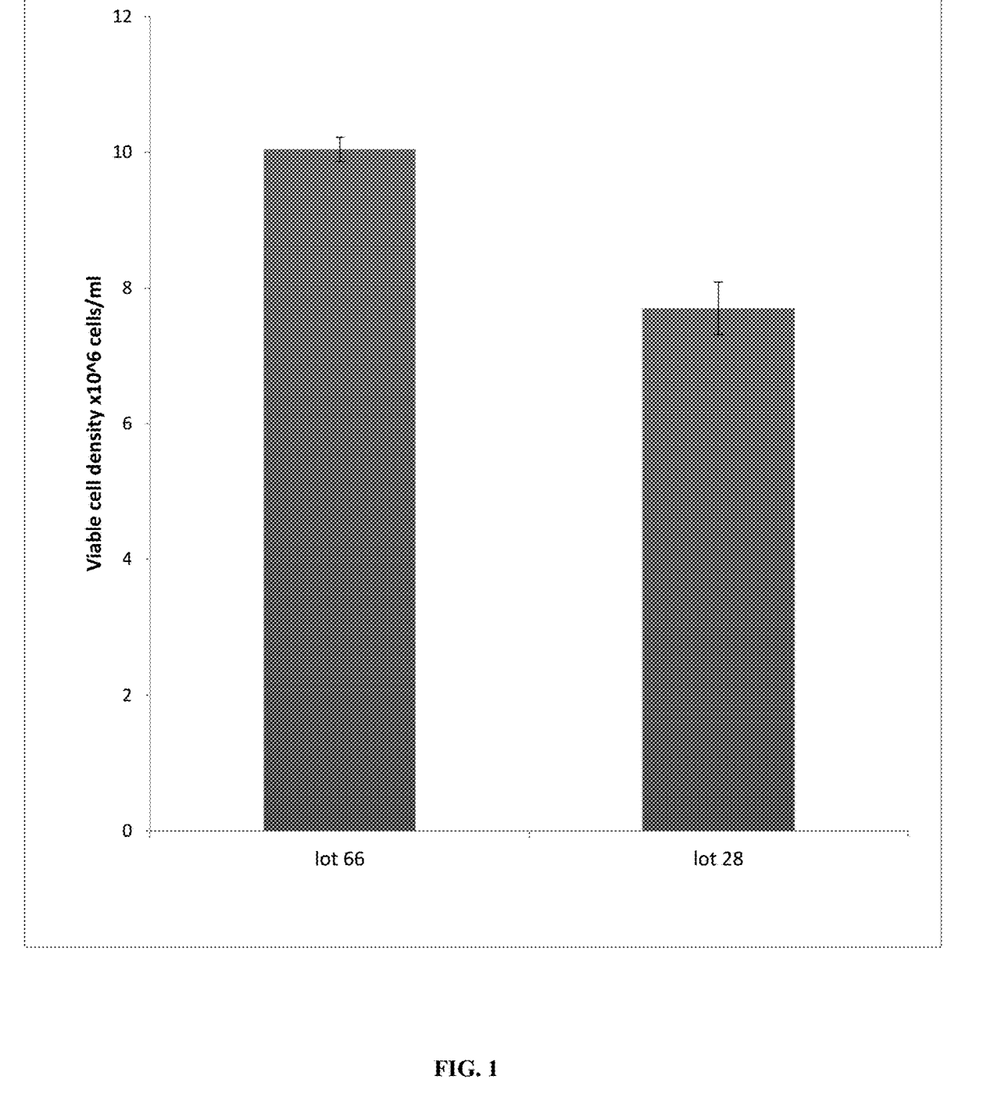
FIG. 1: Cell growth after 4 days in different lots of CD-CHO media (lot 66 and lot 28). Error bars represent standard deviations from duplicate flasks.

The invention is based on the finding that the environmental response of a reference cell in a cell culture media to a plurality of individual cell stressor molecules can act as a fingerprint or signature that is unique to the media and can be used as a means of determining the composition or performance of the media, in particular identifying the media or determining changes or variation in the composition of the media between different media lots or determining stability of the media during storage. This is demonstrated in FIGS. 1 and 2: in FIG. 1, different lots of the same brand of cell culture media are tested with respect to cell growth characteristics and shown to have quite distinct growth performance in shake flask culture over a culture period of greater than four days (FIG. 1). The lots are then rapidly profiled in microtitre plate culture using the method of the invention in under three days and the fingerprints obtained are shown to be distinct. Thus, the fingerprinting method can detect subtle, but functionally important, differences between different batches of cell culture media in a rapid high-throughput manner, and predict functional differences between lots in production culture. While it is not shown in the data, the functional difference are probably reflective of subtle compositional differences between the different lots of media. Compared with the methods of the prior art which require use of expensive and complicated NMR or Raman spectroscopy equipment and expertise, the methods of the invention can be performed in wells of a microtitre plate using fluorescence spectroscopy. The methods of the invention are resultingly easier and less expensive than those of the prior art, and are amenable to multiplex analysis in the wells of the microtitre plate.

In one application of the invention, a cell culture media may be processed by incubating an aliquot of the media with a reference cell and each of a plurality of cell stressor molecules, measuring an environmental response of the reference cell to each cell stressor in the test media, and generating an environmental response signature or fingerprint for the reference cell comprising the plurality of environmental responses that is unique to the test media (media-specific environmental response fingerprint). The fingerprint may thus act as a reference fingerprint for that media, and be used to subsequently determine whether a query media is the same as the test media, or determine or predict whether a different batch (lot) of the test media has the same composition or functionality, or determine whether the composition of the test media has changed during storage or during processing. To determine the composition or performance of a query media, it is incubated with the same reference cell and a plurality of the same reference cell stressor molecules, and a query media specific environmental response fingerprint is obtained for the media. The query fingerprint may then be compared with reference fingerprint for the test media to determine the identity, composition or functional performance of the query media, or to identify or predict compositional or functional performance variation between different batches (lots) of the same cell culture media.

In a first aspect, the invention provides a method of generating a cell culture media-specific environmental response fingerprint; comprising the steps of:
  incubating a reference cell with an aliquot of the cell culture media and at least three chemical cell stressors;
  determining an environmental response of the reference cell in the presence of the cell culture media and each of the plurality of chemical cell stressors; and
  generating a cell culture media specific environmental response fingerprint comprising the plurality of chemical cell stressor specific environmental responses.

Such cell culture media specific environmental response fingerprints can be generated for a reference media (for example a specific brand of media) and then used as a reference fingerprint to subsequently determine whether further batches of the same brand of media are compositionally different to the reference media. Thus, if the reference media is known to be compositionally correct, or to have the required performance characteristics, the environmental response fingerprint for the reference media can be used to determine whether a further batch or lot of the same media has the same composition or predict if it will have the same performance characteristics.

Typically, the environmental response fingerprint is selected from a growth response fingerprint and a production titer response fingerprint.

Suitably, each of the chemical cell stressors stressors is provided at a concentration of 0.5 to 2×IC50.

In a second aspect, the invention provides a method of determining variation between a query cell culture media and a reference cell culture media, the method comprising the steps of:
  (a) generating an environmental response fingerprint specific for query cell culture media according to a method of the invention;
  (b) comparing the query cell culture media-specific environmental response fingerprint of step (a) with a reference media-specific environmental response fingerprints corresponding to a reference cell culture media (optionally having a known characteristic) and generated using the reference cell; and
  (c) determining variation between the query cell culture media and the reference cell culture media based on the level of correlation between the query cell culture media-specific environmental response fingerprint and the reference media-specific environmental response fingerprints.

Suitably, the query cell culture media is a first lot of a specific cell culture media and the reference cell culture media is a second lot of a specific cell culture media.

Typically, the query cell culture media is an unknown cell culture media and the reference cell culture media is a known cell culture media, and in which the method is a method of identifying the unknown cell culture media.

Preferably, the reference cell culture media is a first media and in which the query cell culture media is the first media that has been stored for longer than the reference media, and in which the method is a method of determining storage-induced variation in the first media.

Typically, the variation detected between query and reference cell culture medias is selected from compositional variation, functional variation, or both.

The invention also provides a system for determining a characteristic of a query cell culture media, the system comprising:
  a device comprising a plurality of reaction chambers;
  optionally, a plurality of chemical cell stressors preferably disposed individually within the reaction chambers;
  a determination system for determining the environmental response of a reference cell in the presence of the query cell culture media and each of the plurality of chemical cell stressors; optionally, a storage system for storing a query media-specific environmental response fingerprint corresponding to the plurality of environmental responses of the cell in the presence of the query media and each of the plurality of chemical cell stressors;
  a comparison system configured to compare the query media specific environmental response fingerprint with one or more reference media-specific environmental response fingerprints; and optionally, an output system for displaying an output of the comparison step.

Preferably, the device is a microtitre plate.

Typically, the determination system comprises a microtitre plate reader configured to detect an environmental response of the reference cells in the wells of the microtitre plate.

Suitably, the comparison system comprises a computational model configured to input an environmental response fingerprint corresponding to the query cell culture media, compare the query media environmental response fingerprint with one or more reference media-specific environmental response fingerprints, and output a content based in part of the comparison result.

In one embodiment, the one or more reference media-specific environmental response fingerprints are stored locally on the storage system.

In another embodiment, the one or more reference media-specific environmental response fingerprints are stored on a remote server and accessible through the internet.

DETAILED DESCRIPTION OF THE INVENTION

In this specification, the term "cell culture media" refers to the media and feed products used for the purpose of culturing cells. Examples of cell culture media are GIBCO and DMEM cell culture media sold by Life Technologies, CELLVENTO cell culture media and feeds sold by Merck Millipore, cell culture media products sold by Biological Industries, BIOWHITTAKER media sold by Lonza.

In this specification, the term "query cell culture media" refers to a first cell culture media and the term "reference cell culture media" refers to cell culture media that may be the same or different to the first cell culture media and against which the query cell culture media is being compared to determine any variation between the query cell culture media and the reference cell culture media. Thus, for example the query cell culture media may be a first lot of a specific cell culture media and the reference cell culture media may be a second lot of the specific cell culture media. In another example, the query cell culture may be an unknown cell culture media and the reference cell culture media may be a known cell culture media. In one embodiment, the query media is a first lot of a batch of cell culture media and the reference media is a second lot of the same batch of cell culture media. In another embodiment, the query and reference cell culture medias may be the same media with the exception that one has been stored for a longer period of time that the other (in which case the method of the invention can detect storage-induced variation).

In this specification, the term "reference cell" refers to any cell type, including prokaryotic or eukaryotic cells. Suitably, the cell is a eukaryotic cell, ideally a mammalian cell. Typically, the cell is a producer cell, preferably a mammalian producer cell. The cell may be clonally-derived or non-clonal. In a preferred embodiment, the cell is a clone from a panel of clonal cells, derived from a single parental cell population or derived from different transfected cells. The cell may also be from a distinct cell line, for example a genetically modified cell (i.e. cells with "knock-out" or "knock-in" mutations. The cell line may also be derived by directed evolution, by selection of cells which have adapted to a specific environment of interest. In the methods of the invention that involve a step of correlating a first (query) media-specific environmental response fingerprint with a second (reference) media-specific environmental response fingerprint, it is generally important that these fingerprints are generated using the same reference cell.

In this specification, the term "identifying a cell" should be understood to mean identification of an unknown cell, or confirming the identity of a cell of known or suspected identity.

The invention involves incubating a reference cell with a specific cell culture media and each of a plurality of cell stressor molecules. This means that the cell and specific media is incubated with each of the cell stressor molecules individually, to obtain a growth response of the cell in the presence of each cell stressor molecule. Incubation of the cell with the cell stressor molecule may be performed in any suitable reaction vessel, for example in the wells of a microtitre plate. In one embodiment of the invention, the methods are performed in static microplate culture. Typically, the assay involves mixing a cell sample with a chemical cell stressor and specific cell culture media, and incubating the mixture from 1 to 4 days, and assaying the level of an environmental response of the cells, for example growth or production titer. Suitably, the cell sample is provided at a concentration of from 0.1 to $1.0 \times 10^6$ cells per ml of mixture. Typically, the cell stressor is provided at a concentration of 0.5 to 2×IC50, ideally about 1×IC50. Suitably, the growth of each clone is assayed after a period of incubation of less than 5 days, 4 days, 3 days or 2 days. Ideally, the growth of each clone is assayed after a period of incubation of between 1-4 days, and ideally after 2 and 3 days. Preferably, the environmental response of the reference cells is assayed simultaneously.

The term "cell stressor molecule" or "cell stressor" should be understood to mean a molecule or compound that causes a reduction in cell growth via one or more of multiple cellular pathways. Typically, the plurality of chemical cell stressors are selected from the group consisting of amino acid transport inhibitors, cell cycle inhibitors, a source of carbon, a source of osmotic stress, a source of oxidative stress, an inducer of apoptosis, metabolic effectors, a pH modifier, an inhibitor of glycolysis, and a toxin. Typically, the plurality of chemical cell stressors include stressors selected from at least 4, 5, 6 or 7 of the groups consisting of amino acid transport inhibitors, cell cycle inhibitors, a source of carbon, a source of osmotic stress, a source of oxidative stress, an inducer of apoptosis, metabolic effectors, a pH modifier, an inhibitor of glycolysis, and a toxin. The chemical cell stressors are preferably chemicals that cause a reduction in cell growth via one or more of multiple cellular pathways. Suitably, the plurality of chemical cell stressors comprise at least 2, 3, 4, 5, or 6 functionally diverse chemical cell; stressors, for example at least 3, 4, 5, 6, 7, 8, 9, 10, 12, 14, 16, 18, 20, 21, 22, 23, 24, or 25 different stressors. Typically, the plurality of chemical cell stressors are selected from the group consisting of amino acid transport inhibitors, cell cycle inhibitors, a source of osmotic stress, a source of oxidative stress, an inducer of apoptosis, metabolic effectors, a pH modifier, an inhibitor of glycolysis, and a toxin. These are examples of functionally diverse chemical cell stressors. Typically, the plurality of chemical cell stressors include stressors selected from at least 4, 5, 6 or 7 of the groups consisting of amino acid transport inhibitors, cell cycle inhibitors, a source of osmotic stress, a source of oxidative stress, an inducer of apoptosis, metabolic effectors, a pH modifier, an inhibitor of glycolysis, and a toxin.

In this specification, the term "plurality" as applied to cell stressor molecules should be understood to mean at least three different cell stressor molecules. Typically, the term refers to at least 4, 5, 6, 7, 8, 9, 10, 11, 12, 13, 14, 15, 16, 17, 18, 19 or 20 different cell stressor molecules. Thus, the method of the invention may be performed by employing as few as three distinct cell stressor molecules to generate the cell-specific growth response fingerprint, for example: $CoCl_2$, NAV and MSB; Cadm, MSB and 2DG; and Cadm, dphe, MeiAB.

The term "environmental response" refers to a growth response of the reference cell or a production titre response of the reference cell. The term "growth response" refers to the growth of the reference cell in the presence of a cell stressor molecule. The term "production titer response" refers to the amount of a specific protein, generally a recombinant protein, and ideally a recombinant monoclonal antibody, that the sreference cell generates over a defined time period. The titer may be quantified in absolute or relative terms. Generally titre is referred to as weight of product per volume of culture–grams per litre (g/L) is a common metric (Max titer). Generally, the reference cell is incubated for a specific time period, for example 2-4 days, and following the incubation period a sample of the supernatant is typically taken and assayed for production titer. Various methods will be apparent to the person skilled in the art for measuring production titer, including HPLC and quantitative ELISA.

Typically, the environmental response is a normalised environmental response, which is determined by measuring the environmental of the reference cell in the presence and absence of the cell stressor molecule and determining the difference in growth response due to the presence of the cell stressor molecule. Growth of cells or production titer may be determined using any technique known in the art. In one embodiment, a dye is added to the incubation mixture and a signal emitted by the dye is monitored over time and correlated with growth. For example, a fluorescent or phosphorescent dye may be employed. Examples of suitable dyes are redox dyes, such as Presto Blue®. (Invitrogen, Paisley, UK)

The term "environmental response fingerprint" refers to a plurality of environmental responses for the cell obtained by reacting the cell with a plurality of cell stressor molecules individually in the presence of the same cell culture media. The fingerprint may be embodied as a plurality of environmental response values, or may be embodied in the form of a graph or any other type of visual presentation such as a pattern.

The term "characteristic of a query cell culture media" refers to a compositional characteristic or a functional characteristic of a query cell culture media. Examples of compositional characteristics include identity (i.e. identifying a query media or unknown identity or origin), compositional variation (i.e. identifying compositional variation of a first lot of cell media compared to a second lot, or a reference lot of known composition), stability (i.e. identifying change in composition in a single lot over a time period or as a result of processing). Examples of functional characteristics include performance (for example growth response or production titer response).

The term "cell culture media-specific environmental response fingerprint" or "query culture media-specific environmental respone fingerprint" refer to an environmental response fingerprint or signature that is specific or unique to a specific or query cell culture media. The term "reference media specific environmental response fingerprint" refers to an environmental response fingerprint generated using a reference cell culture media. Generally, the query and reference growth response fingerprints will be generated using the same set of cell stressor molecules.

One aspect of the invention involves comparing a query media-specific environmental response fingerprint with one or more reference media-specific environmental response fingerprints to identify a match or level of correlation between the query and reference environmental response fingerprint(s). Various methods may be employed to match or correlate or compare a query fingerprint with one of the reference fingerprints including mathematical modelling, pattern recognition, or by visual inspection. For example, the environmental responses for a reference cell in the presence of an unknown cell media may be plotted against cell stressors to provide a graph representing the environmental response fingerprint for the query media, and the environmental response fingerprint may be compared visually with the reference environmental response fingerprints corresponding to a specific batch or lot of a cell culture media provided in the same format to identify a level of correlation between the fingerprints and thereby identify the query media. In a preferred embodiment, the comparison step may be performed by mathematical modelling using 'Linear discriminant analysis' and 'nearest neighbour elucidian distance minimisation', using a subset of the chemical growth responses.

Typically, the model employs a 'within groups' leave one out method. With this, 'training data' is optionally made by leaving one out for each group (i.e. 10 samples) and then building an LDA model, and then predicting the cell type for each of the 10 distinct cell types which were left out. Other methods of matching or correlating a query fingerprint with one or more reference fingerprint(s) involves simple Euclidian matching or hierarchical cluster analysis.

The invention also provides a system or kit for identifying a cell. The system or kit typically comprises a device having a plurality of reaction chambers. Preferably, the device is a microtitre plate, typically a microtitre plate having at least 12, 24, 48, or 96 wells.

The system or kit typically comprises a plurality of cell stressor molecules. Preferably, the cell stressor molecules are disposed individually within the wells of the microtitre plate, and are preferably adhered to the wells of the microtitre plate.

The system or kit comprises a determination system for determining the growth response of the cell in the presence of each of the plurality of chemical cell stressors. Typically, the determination system comprises a microtitre plate reader configured to detect and environmental response such as growth of cells or production titer in the wells of the microtitre plate. Suitable microtitre plate readers are commercially available, and are sold by the company BMG. The determination system typically has computer executable instructions to provide e.g., growth response data in computer readable form.

The system or kit also comprises a storage system and a comparison system. These functional modules can be executed on one, or multiple, computers, or by using one, or multiple, computer networks. The determination system has computer executable instructions to provide e.g., sequence information in computer readable form.

The information determined in the determination system can be read by the storage system. As used herein the "storage system" is intended to include any suitable computing or processing apparatus or other device configured or adapted for storing data or information. Examples of an electronic apparatus suitable for use with the present invention include a stand-alone computing apparatus, data telecommunications networks, including local area networks (LAN), wide area networks (WAN), Internet, Intranet, and Extranet, and local and distributed computer processing systems. Storage devices also include, but are not limited to: magnetic storage media, such as floppy discs, hard disc storage media, magnetic tape, optical storage media such as CD-ROM, DVD, electronic storage media such as RAM, ROM, EPROM, EEPROM and the like, general hard disks and hybrids of these categories such as magnetic/optical storage media. The storage system is adapted or configured for having recorded thereon environmental response information and environmental response fingerprint information. Such information may be provided in digital form that can be transmitted and read electronically, e.g., via the Internet, on diskette, via USB (universal serial bus) or via any other suitable mode of communication.

The storage system may have reference environmental response or environmental response fingerprint information stored thereon. As used herein, "stored" refers to a process for encoding information on the storage device. In one embodiment the reference data stored in the storage device to be read by the comparison module is compared, e.g., comparison of a query media specific environmental response fingerprint with a set or panel of reference media-specific environmental response fingerprints.

The "comparison system" can use a variety of available software programs and formats for the comparison operative to compare query growth response fingerprint with reference growth response fingerprints and identify a "match". In one embodiment, the comparison module is configured to use pattern recognition techniques to compare information from one or more entries to one or more reference data patterns. The comparison module may be configured using existing commercially-available or freely-available software for comparing patterns, and may be optimized for particular data comparisons that are conducted. The comparison module provides computer readable information related to the genotype of the sample. Preferably, the comparison system employs a computational model for comparison purposes.

The comparison module, or any other module of the invention, may include an operating system (e.g., UNIX) on which runs a relational database management system, a World Wide Web application, and a World Wide Web server. World Wide Web application includes the executable code necessary for generation of database language statements (e.g., Structured Query Language (SQL) statements). Generally, the executables will include embedded SQL statements. In addition, the World Wide Web application may include a configuration file which contains pointers and addresses to the various software entities that comprise the server as well as the various external and internal databases which must be accessed to service user requests. The Configuration file also directs requests for server resources to the appropriate hardware—as may be necessary should the server be distributed over two or more separate computers. In one embodiment, the World Wide Web server supports a TCP/IP protocol. Local networks such as this are sometimes referred to as "Intranets." An advantage of such Intranets is that they allow easy communication with public domain databases residing on the World Wide Web (e.g., the GenBank or Swiss Pro World Wide Web site). Thus, in a particular preferred embodiment of the present invention, users can directly access data (via Hypertext links for example) residing on Internet databases using a HTML interface provided by Web browsers and Web servers.

The comparison module typically provides a computer readable comparison result that can be processed in computer readable form by predefined criteria, or criteria defined by a user, to provide a content based in part on the comparison result that may be stored and output as requested by a user using a display system.

In one embodiment of the invention, the content based on the comparison result is displayed on a computer monitor. In one embodiment of the invention, the content based on the comparison result is displayed through printable media. The display module can be any suitable device configured to receive from a computer and display computer readable information to a user. Non-limiting examples include, for example, general-purpose computers such as those based on Intel PENTIUM-type processor, Motorola PowerPC, Sun UltraSPARC, Hewlett-Packard PA-RISC processors, any of a variety of processors available from Advanced Micro Devices (AMD) of Sunnyvale, Calif., or any other type of processor, visual display devices such as flat panel displays, cathode ray tubes and the like, as well as computer printers of various types.

In one embodiment, a World Wide Web browser is used for providing a user interface for display of the content based on the comparison result. It should be understood that other modules of the invention can be adapted to have a web browser interface. Through the Web browser, a user may construct requests for retrieving data from the comparison module. Thus, the user will typically point and click to user interface elements such as buttons, pull down menus, scroll bars and the like conventionally employed in graphical user interfaces.

DETAILED DESCRIPTION OF THE INVENTION

Experimental

Two different batches of "CD-CHO media" (Invitrogen, Paisley, UK) were obtained. A CHO cell line was grown in these three media for 3 passages in 30 ml shake flask culture. "Presto Blue" (Invitrogen, Paisley, UK) was mixed 1:1 with CD-CHO media and 20 ul of this was added to each well. The plate was machine shaken and subsequently incubated for 30 minutes at 37 C in a static humidified incubator. After incubation the fluorescence of the wells was measured (excitation 535 nm emission 620 nm) using a fluoroskan ascent (Thermo-Fisher, Loughborough, UK) plate reader. It has been demonstrated prior that fluorescence is linearly correlated with viable cell density in the wells. The results are presented in FIG. 1. It is clear here that there were significant differences in the cell growth in these different batches of media. This was clearly significant from day 4 onwards.

To test the effect this had on the chemical fingerprint, CHO cells were sub-cultured in CD-CHO in either lot number (66) or (28) for 3 passages. Chemical fingerprinting plates were set up in duplicate to determine the growth of cells in the presence of specific cellular stressors The plurality of cell stressor molecules employed were:
2-aminobicyclo-(2,2,1)heptane-carboxylic acid (BCH)
D-phenylalanine-(D-Phe)
α-(methylamino)isobutyric acid (MeAIB)
Sodium Butyrate (NaBu)
Cycloheximide
Ammonium chloride
Cadmium acetate hexhydrate
Cobalt chloride (CoCl$_2$)
Sodium Chloride (NaCl)
Sodium lactate (Na Lac)
Aminotriazole (AMT)
Menadione Sodium Bisulphite (MSB)
Buthionine Sulfoximine (BSO)
Mercaptosuccinic Acid (MS)
2,4,Dinitrophenol (24DNP)
Sodium Oxamate
2-deoxyglucose (2dg)
Dichloroacetate (DCA)
Valproic acid (Val)
Sodium Orthovandate (NaV)
Citric acid
FK866
Brefeldin A (bref)
Rapamycin (Rapa)

Using the same CHO cell line used above for the growth studies, inhibitory dose 50 (IC50) concentrations of the above chemicals were identified through growth studies. Here IC50 is defined as the concentration of the chemical, in question, which inhibits normal cell growth by 50% over a 3 day period. Once IC50s were established, 96 well plates were set up containing the above selection of chemicals at the IC50 concentration and including control wells which contained only cell growth media.

Figure 2:
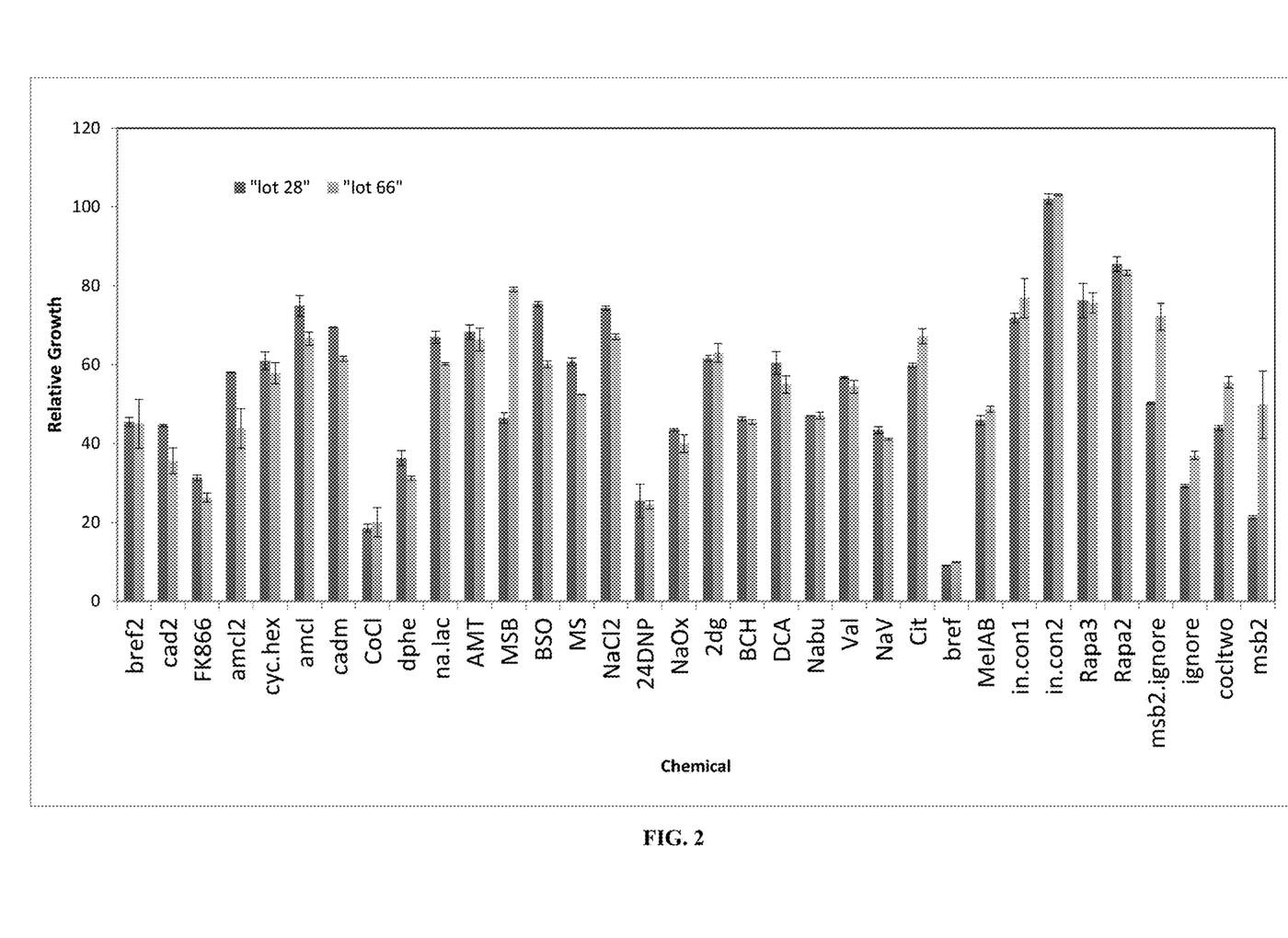
FIG. 2: Chemical fingerprints were taken in the presence of two different lot numbers of CD-CHO media. The y-axis represents the relative growth of the reference cell and the x-axis represents the different chemical cell stressor molecules employed to generate the two media-specific growth response fingerpints (blue and red). Error bars represent standard deviations from duplicate plates.
Figure 3:
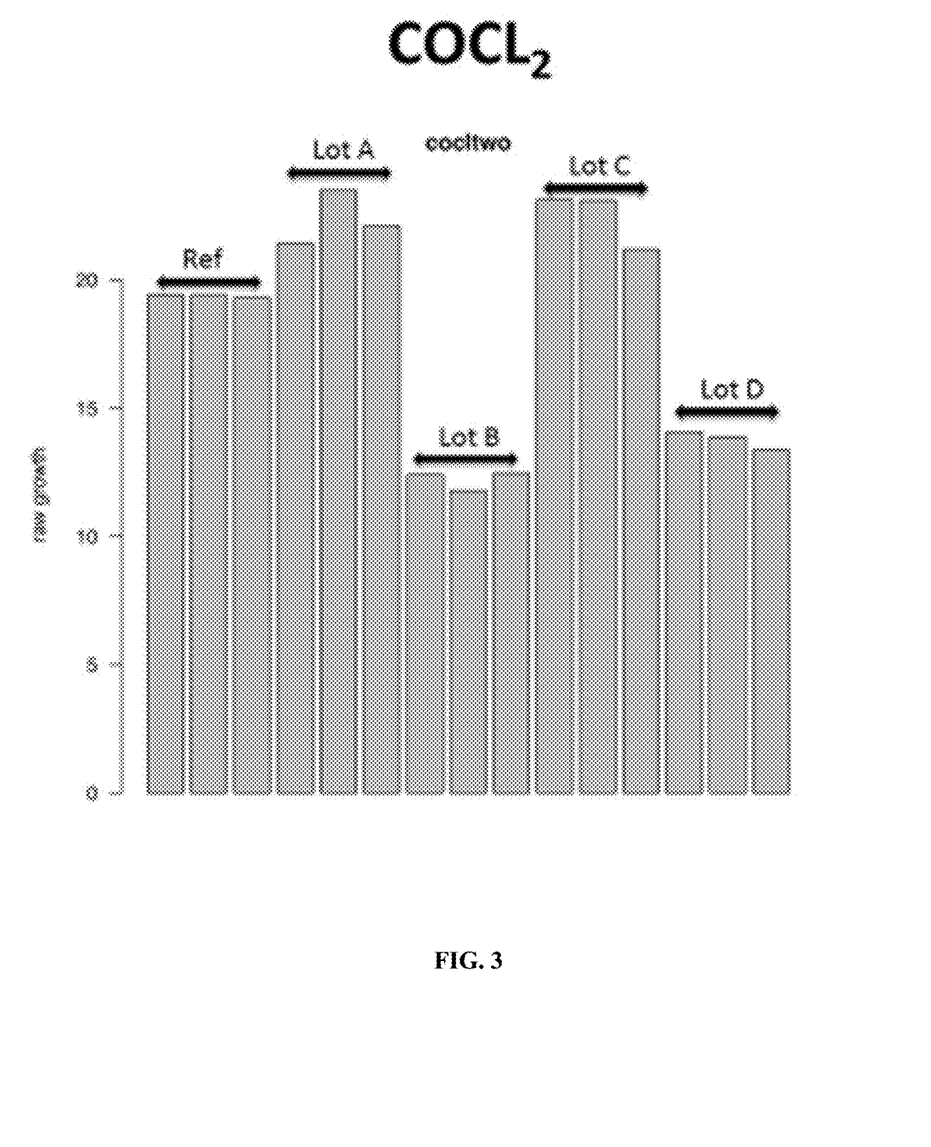
FIG. 3: A reference CHO producer cell was grown in static microplate culture in the presence of cobalt chloride ($CoCL_2$) at an inhibitory concentration and four different lots of the same cell culture media (each lot provided in triplicate). The data shows the differences in growth response of the cell when grown in the different lots of the cell culture media in the presence of the cobalt chloride cell stressor, and demonstrates that chemical cell stressors can be used to differentiate between functionally or compositionally distinct lots of cell culture media.
Figure 4:
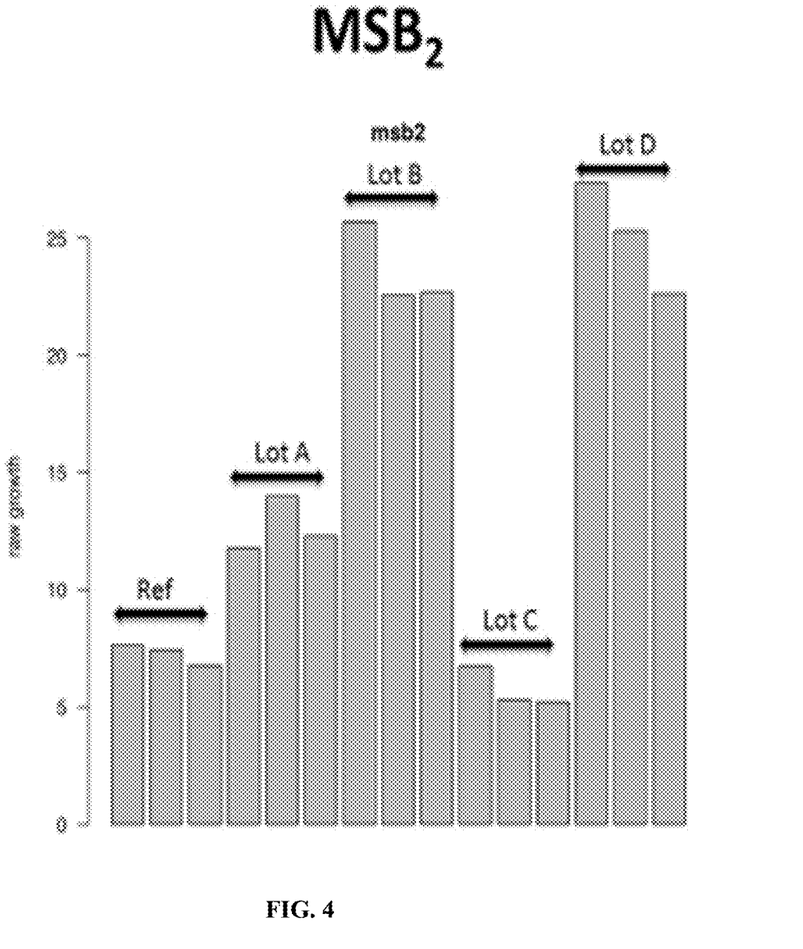
FIG. 4: A reference CHO producer cell was grown in static microplate culture in the presence of menadione sodium bisulphite (MSB2) at an inhibitory concentration and four different lots of the same cell culture media (each lot provided in triplicate). The data shows the differences in growth response of the cell when grown in the different lots of the cell culture media in the presence of the MSB2 cell stressor, and demonstrates that chemical cell stressors can be used to differentiate between functionally or compositionally distinct lots of cell culture media.
Figure 5:
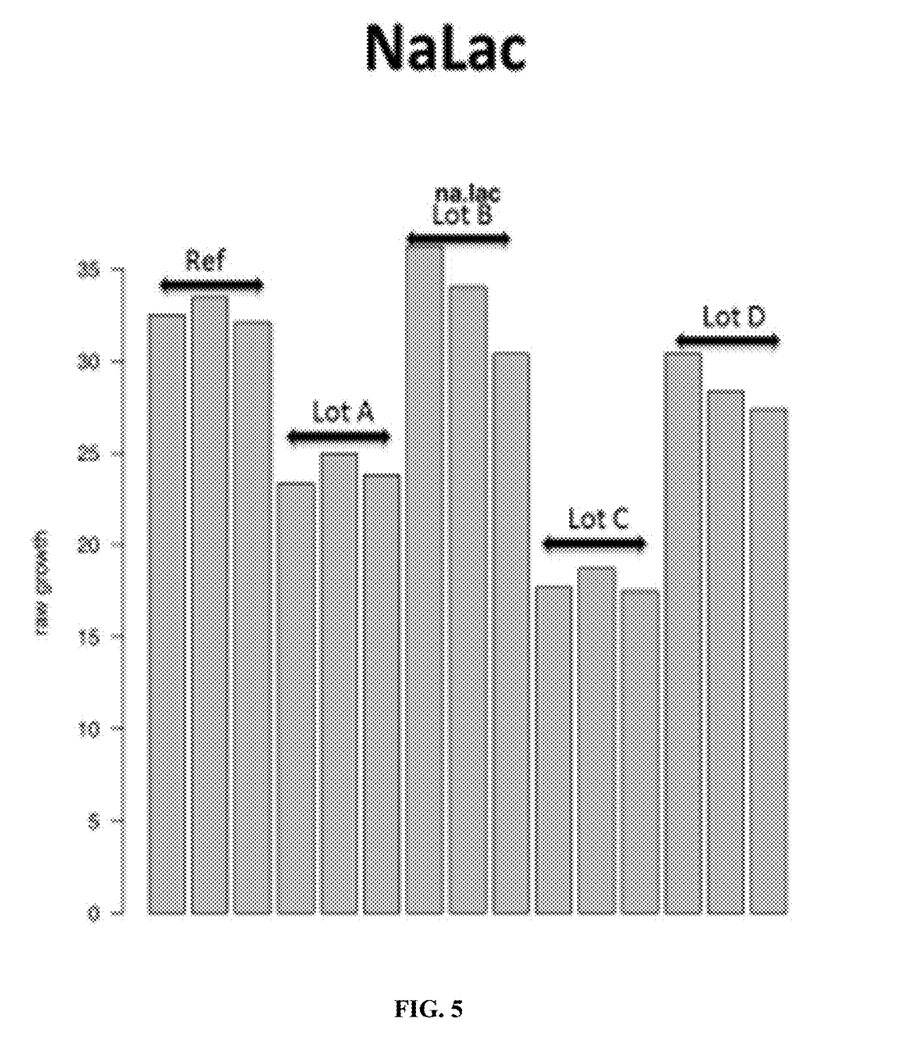
FIG. 5: A reference CHO producer cell was grown in static microplate culture in the presence of sodium lactate (NaLac) at an inhibitory concentration and four different lots of the same cell culture media (each lot provided in triplicate). The data shows the differences in growth response of the cell when grown in the different lots of the cell culture media in the presence of the sodium lactate cell stressor, and demonstrates that chemical cell stressors can be used to differentiate between functionally or compositionally distinct lots of cell culture media.

After this period the level of cell growth in the plates (i.e. in the presence and absence of chemicals as mentioned above) was measured using the "Presto Blue" assay as described above. This allowed a growth fingerprint to be identified for each of the media lots. Here a growth fingerprint is defined as the level of cell growth in each chemical microenvironment relative to the growth of the cells in the control well (i.e. the wells containing just media.). An example of this is illustrated in FIG. 2. From FIG. 2 it is evident that there was a clearly significant difference in the chemical response to MSB. (menandione sodium bisulphate, an inducer of oxidative stress). This is clear with both MSB concentrations. The p-level of significance was <0.05 when adjusting for multiple comparisons (Benjamini-Hockberg).

This demonstrates how subtle differences in media lot composition and functionality can be detected by using a chemical fingerprinting approach.

The invention is not limited to the embodiment hereinbefore described which may be varied in construction and detail without departing from the spirit of the invention.

The invention claimed is:

1. A computer-implemented method of determining variation between a query cell culture media and a reference cell culture media, the computer-implemented method comprising:

generating a query cell culture media-specific environmental response fingerprint of a reference cell, the generating based on incubating the reference cell with an aliquot of the query cell culture media and at least three chemical cell stressors, separately, in wells of a microtiter plate to generate a plurality of chemical cell stressor-specific environmental responses, and determining an environmental response of the reference cell in a presence of the aliquot of the query cell culture media and each of the at least three chemical cell stressors by applying a computational model to the plurality of chemical cell stressor-specific environmental responses generated; and determining the variation between the query cell culture media and the reference cell culture media by applying the computational model to correlate the variation between the query cell culture media-specific environmental response fingerprint and reference media-specific environmental response fingerprints, wherein the query cell culture media is a first lot of a specific cell culture media or known cell culture media and wherein the reference cell culture media is a second lot of a specific cell culture media or known cell culture media.

2. A computer-implemented method as claimed in claim 1, wherein, in an event the query cell culture media is an unknown cell culture media and the reference cell culture media is the known cell culture media, the computer-implemented method is further a computer-implemented method of identifying the unknown cell culture media.

3. A computer-implemented method as claimed in claim 1, wherein, in an event the reference cell culture media is a first media and the query cell culture media is the first media that has been stored for longer than the reference media, and the method is further a method of determining storage-induced variation in the first media.

4. A computer-implemented method as claimed in claim 1, wherein, in an event the query cell culture media is a first lot of specific cell culture media and the reference cell culture media is a second lot of the specific cell culture media, the method is further a method of determining variation between the first and second lots of the specific cell culture media.

5. A computer-implemented method as claimed in claim 1, wherein, in an event the reference cell culture media is a first media and the query cell culture media is the first media that has been stored for longer than the reference media, the method is further a method of determining storage-induced variation in the first media and the variation detected between query and reference cell culture medias is selected from compositional variation, functional variation, or both.

6. A computer-implemented method as claimed in claim 1, wherein the query cell culture media-specific environmental response fingerprint is selected from a growth response fingerprint and a production titer response fingerprint.

7. A computer-implemented method as claimed in claim 1, wherein each of the chemical cell stressor is provided at a concentration of 0.5 to 2×IC50.

8. A computer-implemented method as claimed in claim 1, in which the query cell culture media is a first lot of specific cell culture media and the reference cell culture media is a second lot of the specific cell culture media, and wherein the method is further a method of determining variation between the first and second lots of the specific cell culture media, and wherein the method is still further a method of determining storage-induced variation in the first media and in which the variation detected between query and reference cell culture medias is selected from compositional variation, functional variation, or both.

* * * * *